US009265633B2

(12) United States Patent
Palasis et al.

(10) Patent No.: US 9,265,633 B2
(45) Date of Patent: Feb. 23, 2016

(54) DRUG-ELUTING MEDICAL IMPLANTS

(71) Applicant: 480 Biomedical, Inc., Watertown, MA (US)

(72) Inventors: Maria Palasis, Wellesley, MA (US); Changcheng You, Northbridge, MA (US); Danny Concagh, Medfield, MA (US); Lee Core, Needham, MA (US); Kicherl Ho, Groton, MA (US); Upma Sharma, Somerville, MA (US); Gregory Zugates, Chelmsford, MA (US)

(73) Assignee: 480 BIOMEDICAL, INC., Watertown, MA (US)

( * ) Notice: Subject to any disclaimer, the term of this patent is extended or adjusted under 35 U.S.C. 154(b) by 0 days.

(21) Appl. No.: 14/102,945

(22) Filed: Dec. 11, 2013

(65) Prior Publication Data

US 2014/0100644 A1 Apr. 10, 2014

Related U.S. Application Data

(63) Continuation-in-part of application No. 13/891,574, filed on May 10, 2013, now Pat. No. 9,155,638, and a continuation-in-part of application No. 13/863,632, filed on Apr. 16, 2013, now Pat. No. 8,888,840, application No. 14/102,945, which is a continuation-in-part of application No. 13/766,294, filed on Feb. 13, 2013, now Pat. No. 8,992,601, and a continuation-in-part of application No. 13/370,025, filed on Feb. 9, 2012, now Pat. No. 8,540,765, and a continuation-in-part of application No. 13/253,720, (Continued)

(51) Int. Cl.
| | |
|---|---|
| *A61F 2/90* | (2013.01) |
| *A61F 2/07* | (2013.01) |
| *A61F 2/86* | (2013.01) |
| *A61L 31/06* | (2006.01) |
| *A61L 31/10* | (2006.01) |
| *A61L 31/16* | (2006.01) |
| *D04C 1/06* | (2006.01) |
| *A61K 9/00* | (2006.01) |

(52) U.S. Cl.
CPC ... *A61F 2/86* (2013.01); *A61F 2/90* (2013.01); *A61L 31/06* (2013.01); *A61L 31/10* (2013.01); *A61L 31/16* (2013.01); *D04C 1/06* (2013.01); *A61F 2230/0054* (2013.01); *A61F 2250/0067* (2013.01); *A61K 9/0024* (2013.01); *A61L 2300/416* (2013.01); *A61L 2420/08* (2013.01); *D10B 2403/0112* (2013.01); *D10B 2509/06* (2013.01)

(58) Field of Classification Search
CPC ............... A61F 2/86; A61F 2/90; A61F 2/88; A61L 31/00; A61L 31/16; A61L 31/10
USPC ........................................ 623/1.38, 1.42–1.54
See application file for complete search history.

(56) References Cited

U.S. PATENT DOCUMENTS

| | | | | |
|---|---|---|---|---|
| 6,908,622 | B2 * | 6/2005 | Barry et al. | 424/423 |
| 7,144,422 | B1 * | 12/2006 | Rao | 623/1.42 |
| 7,435,255 | B1 * | 10/2008 | Rao | 623/1.42 |
| 7,803,149 | B2 * | 9/2010 | Bates et al. | 604/509 |
| 7,857,844 | B2 * | 12/2010 | Norton et al. | 623/1.53 |
| 7,875,284 | B2 * | 1/2011 | Reyes et al. | 424/423 |

(Continued)

*Primary Examiner* — Alvin Stewart
(74) *Attorney, Agent, or Firm* — Kacvinsky Daisak Bluni PLLC

(57) ABSTRACT

Disclosed are self-expanding medical implants for placement within a lumen of a patient. The implants comprise a woven or non-woven structure having a substantially tubular configuration, and are designed to be low-profile such that they are deliverable with a small diameter catheter. The implants have a high recoverability and desired mechanical properties.

21 Claims, 4 Drawing Sheets

Related U.S. Application Data filed on Oct. 5, 2011, and a continuation-in-part of application No. 13/183,104, filed on Jul. 14, 2011, now abandoned, and a continuation-in-part of application No. 13/032,281, filed on Feb. 22, 2011, and a continuation-in-part of application No. 12/783,261, filed on May 19, 2010, now Pat. No. 8,137,396.

(60) Provisional application No. 61/624,607, filed on Apr. 16, 2012, provisional application No. 61/179,834, filed on May 20, 2009, provisional application No. 61/227,308, filed on Jul. 21, 2009, provisional application No. 61/251,984, filed on Oct. 15, 2009.

(56) References Cited

U.S. PATENT DOCUMENTS

| | | | |
|---|---|---|---|
| 7,906,133 B2 * | 3/2011 | Barry et al. | 424/423 |
| 8,137,396 B2 * | 3/2012 | Busold et al. | 623/1.38 |
| 8,275,455 B2 * | 9/2012 | Shippy et al. | 604/20 |
| 8,540,765 B2 * | 9/2013 | Palasis et al. | 623/1.38 |
| 2002/0018795 A1 * | 2/2002 | Whitbourne | A61K 9/0024 424/414 |
| 2003/0059454 A1 * | 3/2003 | Barry et al. | 424/423 |
| 2005/0202061 A1 * | 9/2005 | Barry et al. | 424/426 |
| 2005/0278021 A1 * | 12/2005 | Bates | A61F 2/82 623/1.44 |
| 2006/0009835 A1 * | 1/2006 | Osborne et al. | 623/1.13 |
| 2006/0093771 A1 * | 5/2006 | Rypacek et al. | 428/36.91 |
| 2007/0293927 A1 * | 12/2007 | Frank et al. | 623/1.11 |
| 2008/0020013 A1 * | 1/2008 | Reyes | A61F 2/91 424/423 |
| 2008/0050413 A1 * | 2/2008 | Horvers et al. | 424/423 |
| 2008/0167724 A1 * | 7/2008 | Ruane et al. | 623/23.7 |
| 2008/0286325 A1 * | 11/2008 | Reyes et al. | 424/423 |
| 2008/0306592 A1 * | 12/2008 | Wang | 623/11.11 |
| 2009/0182404 A1 * | 7/2009 | Shokoohi | 623/1.11 |
| 2009/0258053 A1 * | 10/2009 | Horvers | A61L 31/10 424/423 |
| 2009/0318848 A1 * | 12/2009 | Shippy, III et al. | 604/20 |
| 2011/0319977 A1 * | 12/2011 | Pandelidis et al. | 623/1.15 |
| 2012/0232640 A1 * | 9/2012 | Horvers | 623/1.11 |
| 2013/0231638 A1 * | 9/2013 | Speck et al. | 604/509 |
| 2013/0303983 A1 * | 11/2013 | Barbick et al. | 604/103.02 |
| 2014/0100644 A1 * | 4/2014 | Palasis et al. | 623/1.2 |
| 2014/0180398 A1 * | 6/2014 | Milner et al. | 623/1.38 |

* cited by examiner

ND LG-ELUTING MEDICAL IMPLANTS

This application is a continuation-in-part of, and claims the benefit of and priority to, U.S. patent application Ser. No. 13/891,574, filed May 10, 2013, U.S. patent application Ser. No. 13/863,632, filed Apr. 16, 2013, which claims the benefit of priority to U.S. Provisional Patent Application No. 61/624,607, filed Apr. 16, 2012; U.S. patent application Ser. No. 13/766,294, filed Feb. 13, 2013, U.S. patent application Ser. No. 13/370,025, filed Feb. 9, 2012; U.S. patent application Ser. No. 13/253,720, filed Oct. 5, 2011; U.S. patent application Ser. No. 13/183,104, filed Jul. 14, 2011; and U.S. patent application Ser. No. 13/032,281, filed Feb. 22, 2011; all of which are continuations-in-part of, and claim the benefit of and priority to U.S. patent application Ser. No. 12/783,261, filed May 19, 2010; which claims the benefit of and priority to 61/179,834, filed May 20, 2009; 61/227,308, filed Jul. 21, 2009; and 61/251,984, filed Oct. 15, 2009, each of which is incorporated herein in their entireties for all purposes.

FIELD OF THE INVENTION

The present invention relates to medical implants, and more specifically, to drug eluting medical implants that are intended for placement within a lumen or cavity of a patient.

BACKGROUND

A variety of medical conditions are treatable by the implantation of tubular devices into natural body lumens. For example, it is commonplace to implant metallic stents into the coronary arteries of patients with heart disease following balloon angioplasty to minimize the risk that the arteries will undergo restenosis. Recently, commercial stents have included drug-eluting polymer coatings that are designed to further decrease the risk of restenosis. Other examples of conventional tubular medical implants include woven grafts and stent-grafts that are used to span vascular aneurysms, polymeric tubes and catheters that are used to bypass strictures in the ureter and urethra, and stents that are used in the peripheral vasculature, prostate, sinus and esophagus. It should be recognized that the size of the devices of the present invention will depend upon their clinical application. For example, stents for the esophagus and other large bodily lumens may be as large as 30 mm or 40 mm in diameter or larger.

Despite the evolution of metallic stents, they continue to have limitations such as the possibility of causing thrombosis, restenosis and vascular remodeling. While the use of biodegradable and biostable polymeric materials for stents and other implantable devices has been proposed to eliminate the possible long-term effects of permanent implants, the use of such materials has been hindered by relatively poor expandability and mechanical properties. For example, the expansion characteristics and radial strength of prototype stents made from biodegradable and biostable polymeric materials has been significantly lower than that of metallic stents. This is particularly the case where such stents are low profile and make use of small diameter fibers or thin walled struts that comprise the stent body. Furthermore, the degradation rate and the manner in which such devices degrade in the body have been difficult to control. Finally, where such devices are used as a drug delivery vehicle, the drug elution rate has been difficult to reproducibly characterize.

There is therefore a need for low-profile, self-expanding implantable tubular devices that have sufficient expansion characteristics, strength and other mechanical and drug release properties that are necessary to effectively treat the medical conditions for which they are used. There is also generally a need to provide such devices that include the lowest possible dose of drug that is able to provide clinically effective results.

SUMMARY

In one aspect, the present invention includes an implantable medical device for placement within a lumen or cavity of a patient. In another aspect, the present invention includes a method of loading the medical device into a delivery catheter just prior to being implanted into a patient. In another aspect, the present invention includes a method of treating a patient by delivering the medical device to a target location within the patient. In yet another aspect, the present invention includes a kit that comprises the implantable medical device.

The devices of the present invention are generally tubular structures made from polymeric or metallic strands as described herein. In certain embodiments, the devices comprise tubular structures comprising polymeric strands, and further comprising a therapeutic agent, such as paclitaxel. The amount of therapeutic agent is within the range of about 0.002 to about 0.175 micrograms per square millimeter of the surface area of the tubular structures.

DESCRIPTION OF PREFERRED EMBODIMENTS

The present invention provides for medical implants that have expansion characteristics and mechanical properties that render them suitable for a broad range of applications involving placement within bodily lumens or cavities. As used herein, "device," "implant," "stent," and "scaffold" are used synonymously. Also as used herein, "self-expanding" is intended to include devices that are crimped to a reduced configuration for delivery into a bodily lumen or cavity, and thereafter tend to expand to a larger suitable configuration once released from the delivery configuration, either without the aid of any additional expansion devices or with the partial aid of balloon-assisted or similarly-assisted expansion. When compared with conventional self-expanding medical implants, the implants of the present invention recover to an exceptionally high percentage of their manufactured diameter after being crimped and held in a small diameter for delivery into a bodily lumen. Moreover, when compared with conventional self-expanding implants and particularly polymeric implants, the implants of the present invention are characterized by much improved strength and other desired mechanical properties. As used herein, "strength" is used to mean the resistance of the medical implants of the present invention to deformation by radial forces. Examples of strength measurements, as used to characterize the medical implants of the present invention, include radial resistive force and chronic outward force, as further defined herein. Also, when compared with conventional drug eluting stents, the implants of the present invention comprise a relatively small quantity of therapeutic agent while are nonetheless able to provide favorable preclinical results. A low quantity of therapeutic agent is desirable for numerous reasons, such as to reduce the manufacturing cost and to minimize the possibility of producing unintended effects in tissues adjacent to the target tissue to be treated.

Figure 1:
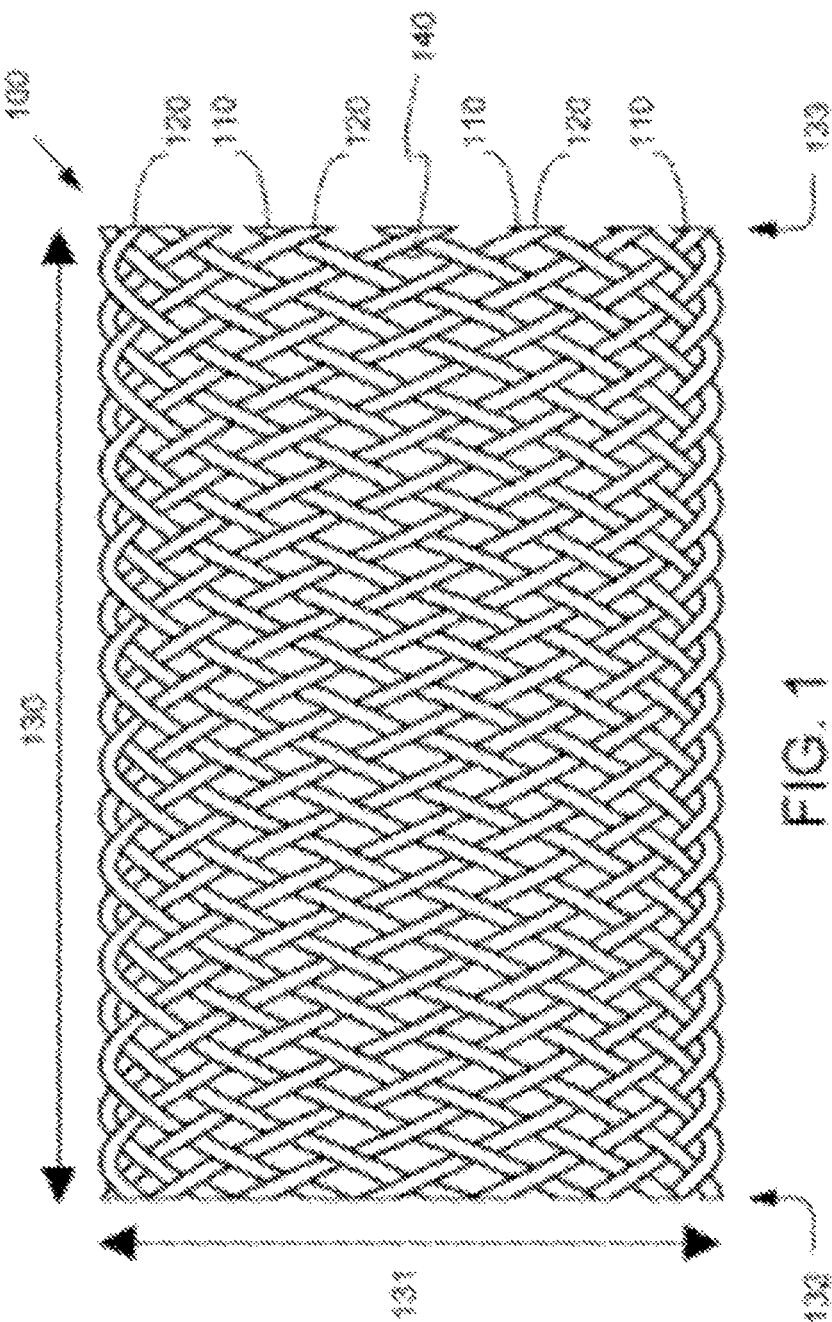
FIG. 1 is a side view of an implantable braided medical device, in accordance with an embodiment of the present invention.

In one embodiment shown in FIG. 1, the implant 100 preferably comprises at least one strand woven together to form a substantially tubular configuration having a longitudinal dimension 130, a radial dimension 131, and first and second ends 132, 133 along the longitudinal dimension. As used herein, "strand," "fiber," and "strut" are used synonymously to mean the elements that define the implant configuration. As used herein, "woven" is used synonymously with "braided." For example, the tubular configuration may be woven to form a tubular structure comprising two sets of strands 110 and 120, with each set extending in an opposed helix configuration along the longitudinal dimension of the implant. The sets of strands 110 and 120 cross each other at a braid angle 140, which may be constant or may change along the longitudinal dimension of the implant. Preferably, there are between about 16 and about 96 strands used in the implants of the present invention, more preferably between about 16 and about 32 strands, and the braid angle 140 is within the range of about 90 degrees to about 135 degrees throughout the implant. The strands are woven together using methods known in the art, using known weave patterns such as Regular pattern "1 wire, 2-over/2-under", Diamond half load pattern "1 wire, 1-over/1-under", or Diamond pattern "2 wire, 1-over/1-under".

The strands are preferably made from at least one biodegradable material that is preferably fully absorbed within about two years of placement within a patient, and more preferably within about one year of placement within a patient. In some embodiments, the strands are fully absorbed within about six or fewer months of placement within a patient. The first and second strand sets 110, 120 may be made from the same or different biodegradable polymer. In other embodiments, the first and/or second strand sets 110, 120 may be made from biodegradable metallic materials such as magnesium or zinc, or from biostable metallic materials such as stainless steel, chromium-cobalt alloys, or other suitable biocompatible materials. Non-limiting examples of biodegradable polymers that are useful in the at least one strand of the present invention include poly lactic acid (PLA), poly glycolic acid (PGA), poly trimethylene carbonate (PTMC), poly caprolactone (PCL), poly dioxanone (PDO), and copolymers thereof. Preferred polymers are poly(lactic acid co-glycolic acid) (PLGA) having a weight percentage of up to about 20% lactic acid, or greater than about 75% lactic acid (preferably PLGA 88:12 (wt:wt)), with the former being stronger but degrading in the body faster. The composition of PLGA polymers within these ranges may be optimized to meet the mechanical property and degradation requirements of the specific application for which the implant is used. For desired expansion and mechanical property characteristics, the materials used for the strands preferably have an elastic modulus within the range of about 1 to about 10 GPa, and more preferably within the range of about 6-10 GPa.

The strands used in the implant 100 preferably have a cross-sectional diameter in the range of from about 0.003 inches to about 0.007 inches, with embodiments including 0.003, 0.004, 0.005, 0.006 and 0.007 inches, and intervals therebetween. Where multiple strands are used, they may be of substantially equal diameters within this range, or first strand set 110 may be of a different general diameter than second strand set 120. In some embodiments, multiple strand sets are used with different diameters such that the implant includes three, four or more different diameter strands. In either event, the diameters of strands are chosen so as to render the implant 100 preferably deliverable from a 10 French delivery catheter (i.e., 3.3 mm diameter) or smaller, and more preferably from a 7 French delivery catheter (i.e., 2.3 mm diameter) or smaller. The ability to place the implant of the present invention into small diameter delivery catheters allows for its implantation into small diameter bodily lumens and cavities, such as those found in the vascular, biliary, uro-genital, iliac, and tracheal-bronchial anatomy. Exemplary vascular applications include coronary as well as peripheral vascular placement, such as in the superficial femoral artery (SFA). It should be appreciated, however, that the implants of the present invention are equally applicable to implantation into larger bodily lumens, such as those found in the gastrointestinal tract, for applications such as esophageal scaffolds.

Figure 2:
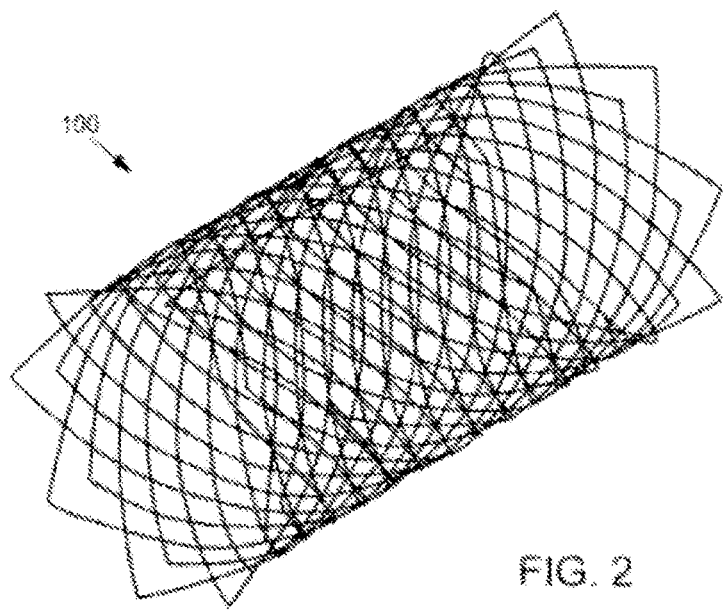
FIG. 2 is a side view of an implantable unitary framework medical device, in accordance with an embodiment of the present invention.

In another embodiment of the present invention, the implant is a non-woven, self-expanding structure, such as a unitary polymeric framework. As shown in FIG. 2, the non-woven implant 100 is preferably characterized by a regular, repeating pattern such as a lattice structure. The use of a unitary framework may provide a reduced profile when compared to the use of woven strands, which yield a minimum profile that is the sum of the widths of overlapping strands. In addition, a unitary framework eliminates the possible change in length of the implant associated with crimping and subsequent expansion, known as foreshortening, which is common in braided stents. When the implant 100 is a unitary framework, it is fabricated using any suitable technique, such as by laser cutting a pattern into a solid polymer tube. In a preferred embodiment, when the implant 100 is a unitary framework, it is formed by laser cutting and includes a wall thickness of between about 75 and about 100 microns. It should be recognized that while the present invention is described primarily with reference to woven strand configurations, aspects of the present invention are equally applicable to non-woven, self-expanding structures unless necessarily or expressly limited to woven configurations.

Certain embodiments of the present invention make use of 16, 24 or 32 strands. These embodiments are characterized by surface areas as set forth in Table I.

TABLE I

Surface areas of certain embodiments of the present invention.

| No. of strands | Surface area (square millimeters per millimeter of implant length) | | | | |
|---|---|---|---|---|---|
| | 0.003" strands | 0.004" strands | 0.005" strands | 0.006" strands | 0.007" strands |
| 32 | 22.7-24.4 | 30.3-31.6 | 37.9-39.0 | 45.4-46.3 | 53.1-53.8 |
| 24 | 17.1-18.3 | 22.7-23.7 | 28.5-29.2 | 34.1-34.7 | 39.8-40.4 |
| 16 | 11.4-12.2 | 15.1-15.8 | 19.0-19.5 | 22.7-23.2 | 26.5-26.9 |

As can be seen from Table I, certain embodiments of the present invention have surface areas within the range of about 11.4 square millimeters per every millimeter of implant length (in the case of certain embodiments having 16 strands of 0.003" cross-sectional diameter) to about 53.8 square millimeters per millimeter of implant length (in the case of certain embodiments having 32 strands of 0.007" cross-sectional diameter). It should be noted that the embodiments of the present invention included in Table I generally have a braid angle of about 127 degrees, and that varying braid angle and other scaffold attributes may influence surface area.

Figure 3:
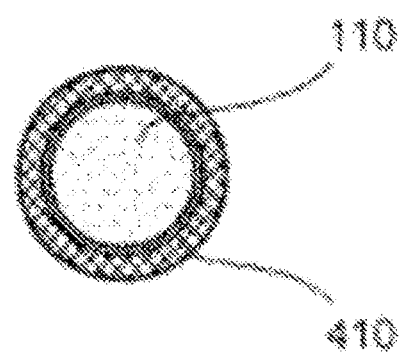
FIG. 3 is a cross-sectional view of a strand of an implantable medical device in accordance with an embodiment of the present invention that includes a support coating.

There are a variety of strengthening means that are useful in the present invention to help provide the expansion and mechanical properties that are needed to render the implant 100 effective for its intended purpose. In one embodiment, the strengthening means is a support coating 410 on at least one of the strands of the implant 100. Although referred to herein as a "coating," the support coating 410 does not necessarily coat the entire implant 100, and may not form a discrete layer over the stands or unitary framework of the implant 100; rather, the support coating 410 and underlying strands or unitary framework may be considered as a composite structure. The support coating 410 is made from an elastomeric polymer that, due to its elastic nature when compressed or elongated, applies a force to implant 100 that acts in favor of radial expansion and axial contraction, thus enhancing radial strength. The polymer of the support coating 410 is preferably biodegradable. Alternatively, the support coating 410 is made from a shape memory polymer or a polymer that otherwise contracts upon heating to body temperature. The inventors have surprisingly found that the use of support coatings on the polymeric implants of the present invention can result in the recovery of more than 90% of implant diameter post-crimping, and yield significantly higher radial forces when compared with uncoated implants or even with self-expanding metallic stents. The support coating 410 may be applied as a conformal coating (as shown in cross-section of an individual strand in FIG. 3, a "conformal" coating as used herein is a coating that generally conforms to the shape of the underlying strand), may be partially applied to one or more individual strands such that the support coating 410 is applied to only a portion of the implant along its longitudinal dimension, or may be applied to only the inner or outer diameter of one or more individual strands. Also, the support coating 410 may optionally vary in weight along the length of the implant; for example, the ends of the implant may be coated with a thicker layer than the mid-section to provide added support to the ends of the implant. In addition, the support coating may accumulate at the crossover points or "nodes" of the woven device, which has the effect of aiding in diameter recovery and the achievement of preferred strength characteristics.

Examples of polymer materials used for the support coating 410 include suitable thermoplastic or thermoset elastomeric materials that yield the elongation, mechanical strength and low permanent deformation properties when combined with the implant strand(s). The inventors have found examples of suitable polymers to include certain random copolymers such as poly(lactic acid-co-caprolactone) (PLCL), poly(glycolide-co-caprolactone) (PGCL), and poly (lactic acid-co-dioxanone) (PLDO), poly(butylene succinate) (PBS), poly(p-dioxanone) (PDO), certain homopolymers such as poly trimethylene carbonate (PTMC), and copolymers and terpolymers thereof.

In certain embodiments, such polymers are optionally crosslinked with a crosslinker that is bi- or multi-functional, polymeric, or small molecule to yield a thermoset polymer having a glass transition temperature (Tg) that is preferably lower than body temperature (37° C.), more preferably lower than room temperature (25° C.), and most preferably lower than about 10° C. The thermoset elastomers provide a high elongation to break with low permanent deformation under cyclic mechanical testing.

In one preferred embodiment, the polymer material used for the support coating 410 is a biodegradable thermoset elastomer synthesized from a four arm PGCL polymer having a weight ratio of approximately 50:50 GA:CL that is crosslinked with hexamethylene diisocyanate (HDI) to give a polyester with urethane crosslinks. Without wishing to be bound by theory, the inventors believe that the combination of the elastic segment (polyester portion) and the interactions (such as hydrogen bonding, allophanate or biuret formation) between the urethane segments of such polymers, in addition to a certain crosslinking density, yields preferred properties such as a high degree of elastic recovery under cyclic mechanical strain and high overall elasticity.

In other preferred embodiments, the support coating comprises PLCL having a weight ratio of approximately 50:50 LA:CL. In yet another preferred embodiment, a PLCL 50:50 crosslinked with hexamethylene diisocyanate support coating is applied to a PLGA 88:12 (wt:wt) braided implant.

The polymer material used for support coating 410 may be optimized for desired mechanical properties. For example, the inventors have found that the molecular weight of such polymers may be manipulated to enhance coating performance. As an example, when PLCL 50:50 crosslinked with hexamethylene diisocyanate is used as the support coating of the present invention, the inventors have found that a molecular weight (Mn) between about 30 kDa and 120 kDa, preferably from 33 k to 80 k, results in a lower modulus of elasticity and a higher strain to fracture, thus making the coating better able to adhere to a PLGA braided implant during crimping and post-crimping expansion and therefore less likely to fracture during deployment. Similarly, the inventors have found that when PGCL 50:50 (wt:wt) crosslinked with hexamethylene diisocyante is used as the support coating of the present invention, a molecular weight (Mn) from 8 kDa to 20 kDa does not yield an appreciable change in properties, but that a further increase in molecular weight to 50 kDa results in a four-fold increase in the strain at failure of the coating material. As such, a preferred range of molecular weight (Mn) for PGCL used in the implants of the present invention is about 23 kDa to about 100 kDa. Additionally, the inventors have found that the viscosity of the spray coating solution, the weight percent of crosslinker used in the spray coating solution, and the temperature and duration of the support coating crosslinking process can be optimized to provide preferred coating morphologies and radial forces.

In the event that the support coating 410 comprises a thermoset elastomer polymer, the crosslink density may be varied to yield desired mechanical properties. For example, chain terminators may be used in thermoset elastomeric materials such as polyester urethanes to control crosslink density. The chemical crosslink density is adjusted by using such chain terminators to control the degree of crosslinking taking place during the thermoset curing process. The crosslink density of the resultant elastomers depends on the concentration of chain terminators incorporated into the elastomeric network. Both small molecular agents and polymers may react with chain terminators. In some embodiments, HDI is used as a cross-linker, and the prepolymer is provided in a ratio of between 1:1 and 25:1 wt/wt relative to HDI. Any suitable unreactive organic solvent may be used in the present invention, including dichloromethane (DCM), ethyl acetate, acetone, methyl tert-butyl ether, toluene, or 2-methyltetrahydrofuran. Examples of suitable chain terminators in this embodiment include any suitable monofunctional compound such as monoisocyanates that contain only one of the functional group R—N=C=O, or monoalcohols that contain only one of the functional group R3-OH. Other examples of suitable chain terminators include small molecular agents and polymers that carry one active functional group that may react with either isocyanate or hydroxyl groups, such as but not limited to amines, alcohols, isocyanates, acyl chlorides, and sulfonyl chlorides. The suitable chain terminator is provided in a wide range of amounts (0-20 wt % relative to the prepolymer) to control the cross-linking density. When used with an embodiment of the present invention, the solution of polyester, crosslinker, and chain terminator is dissolved in a solvent and spray coated onto the surface of the implant 100 and cured to form support coating 410 as a conformal elastomeric coating.

The support coating 410 is coated onto the surface of the implant 100 using any suitable method, such as spraying, dipping, electrospraying, rolling, and the like. If implant 100 is a woven structure, the support coating 410 may be applied to individual strands prior to forming the woven structure, or to the woven structure after the formation thereof. In this case, owing to surface tension, the coating preferably collects at intersection points between strands. If implant 100 is a non-woven structure, the support coating 410 may be applied, for example, to a solid polymer tube either before or after the removal of material such as by laser cutting to form a patterned, non-woven structure.

The amount of support coating 410 applied to the implant 100 has been identified as one of the factors that contribute to the expansion characteristics and mechanical strength of the implant. Preferably, the application of the support coating 410 increases the weight of the uncoated implant 100 by about 20% to about 100%, more preferably, by about 24% to about 70%, more preferably by about 30% to about 60%, and more preferably more than about 35%.

In yet another embodiment, the strengthening means includes the incorporation of additives into one or more of the strands. In one example, such additives are neutralizing agents such as calcium salts (e.g., calcium carbonate or calcium phosphate) or other salts such as barium salts that increase the mechanical strength of the strands into which they are incorporated, and further act to neutralize any acidic byproducts resulting from the degradation of the strand material(s). In another example, such additives are plasticizers such as polyethylene glycol (PEG) that dissolve from the strand(s) in-vivo, thus increasing the flexibility of the strand(s) and the implant over time.

In one embodiment, the implant 100 delivers one or more therapeutic agents at the site of implantation. The terms "therapeutic agents" and "drugs" are used herein interchangeably to mean any material that has a therapeutic effect at an implantation site. Also as used herein, the device of the present invention is said to "deliver" or "elute" therapeutic agent—these terms are used synonymously and generally to refer to any mechanism by which the therapeutic agent comes into contact with tissue.

Figure 4:
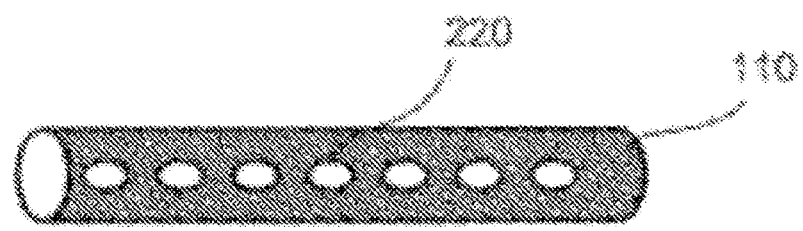
FIG. 4 is a side view of a strand of an implantable medical device in accordance with an embodiment of the present invention that includes discrete areas of therapeutic agent thereon.

The therapeutic agent(s) may be applied to one or more strands for delivery therefrom in a number of ways. In one example, the therapeutic agent(s) are embedded within a conformal polymer coating 210 that adheres to one or more individual strands of the implant 100. Such a coating 210 is preferably made from a biodegradable polymer admixed with the therapeutic agent(s) such that the agent is eluted from the polymer over time, or is released from the coating as it degrades in-vivo. In another example as shown in FIG. 4, one or more therapeutic agents are applied in discrete areas 220 on one or more individual strands (shown as length of individual strand). Like coating 210, discrete areas 220 are preferably made from a biodegradable polymer admixed with the therapeutic agent(s) and eluted from the polymer over time, or are released from the coating as it degrades in-vivo. In either of coating 210 or discrete areas 220, the biodegradable polymer may be the same as or different from the biodegradable polymer(s) used in the strands of the implant. In yet another example, the therapeutic agent(s) are admixed or contained the strand(s) of the implant 100 such that the agent(s) are eluted from the one or more strands over time, or are released from the one or more strands as the strand(s) degrade in-vivo. In yet another example, the therapeutic agent(s) are mixed within the support coating 410 without any additional coating. Likewise, in embodiments in which the implant 100 is a non-woven structure, the therapeutic agent(s) may be admixed with the polymer used to fabricate the implant 100. Generally, the implant designs of the present invention may present a significantly higher surface area, with more closely spaced strands or struts, when compared with conventional metallic stents, thus offering the possibility of a more uniform distribution of drug in the tissue surrounding the implant.

The therapeutic agent(s) used in the present invention are any suitable agents having desired biological effects. In a preferred embodiment, the therapeutic agent used in the present invention is paclitaxel, its analogs, or derivatives thereof.

Figure 5:
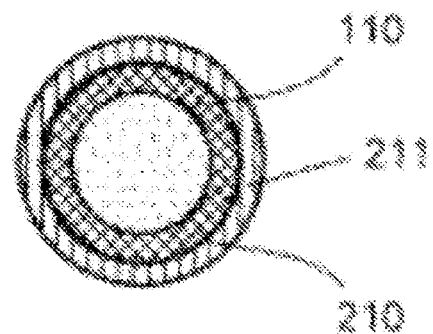
FIG. 5 is a cross-sectional view of a strand of an implantable medical device in accordance with an embodiment of the present invention that includes a therapeutic agent coating and a topcoat.

Coating 210 or areas 220 containing one or more therapeutic agents are applied to implant 100 by any suitable method, such as spraying, electrospraying, rolling, dipping, chemical vapor deposition, and potting. As an alternate embodiment, coating 210 or areas 220 are further coated with a biodegradable or biostable topcoat as shown in FIG. 5 (individual strand shown in cross-section), that acts to regulate the delivery of the therapeutic agent from coating 210 or areas 220 into bodily tissue. In one embodiment, the topcoat 211 acts as a diffusion barrier such that the rate of delivery of the therapeutic agent(s) are limited by the rate of its diffusion through the topcoat 211. In another embodiment, the therapeutic agent(s) cannot diffuse through the topcoat 211 such that delivery thereof is simply delayed until the degradation of the topcoat 211 is complete. The topcoat 211 preferably comprises a biodegradable polymer that is the same as or different from that of the coating 210 or the strands. If implant 100 is a woven structure, coatings 210, 220, or 211 may be applied to individual strands prior to forming into the woven structure, or to the woven structure after the formation thereof. If implant 100 is a non-woven structure, coatings 210, 220, or 211 may be applied, for example, to a solid polymer tube either before or after the removal of material such as by laser cutting to form a patterned, non-woven structure. In embodiments that include support coating 410, the coatings 210, 220, and/or 211 are preferably applied over such support coating 410, or the support coating 410 itself may include the therapeutic agent(s) in lieu of a separate coating 210. Alternatively, the coatings 210, 220, and/or 211 may be applied between the supporting coating 410 and the implant 100.

Preferred embodiments of the present invention comprise the strands listed in Table I, with a conformal coating 210 comprising paclitaxel as therapeutic agent. The paclitaxel is preferably added to the polymer material that comprises the coating 210 before the coating 210 is applied. The inventors have surprisingly found that it is possible to achieve favorable preclinical results from the use of such embodiments in which the drug content of the coating 210 is significantly reduced in comparison to conventional drug-eluting stents. For example, for the embodiments listed in Table I, the inventors have found favorable preclinical results with paclitaxel content specified in Table II:

TABLE II

Paclitaxel content in implants of the present invention.

| No. of strands | Amount of paclitaxel (micrograms per square millimeter of implant surface area) | | | | |
|---|---|---|---|---|---|
| | 0.003" strands | 0.004" strands | 0.005" strands | 0.006" strands | 0.007" strands |
| 32 | 0.004-0.088 | 0.003-0.066 | 0.003-0.053 | 0.002-0.044 | 0.002-0.038 |
| 24 | 0.005-0.117 | 0.004-0.088 | 0.003-0.070 | 0.002-0.059 | 0.002-0.050 |
| 16 | 0.008-0.175 | 0.006-0.132 | 0.005-0.105 | 0.004-0.088 | 0.004-0.075 |

As can be seen from inspection of Table II, embodiments of the implants of the present invention comprise an amount of paclitaxel within the range of about 0.002-0.175 micrograms per square millimeter of implant surface area. In certain preferred embodiments, the implants of the present invention comprise an amount of paclitaxel within the range of about 0.002-0.15, 0.002-0.125, 0.002-0.10, 0.002-0.08, 0.002-0.06, 0.002-0.04, 0.002-0.02, 0.002-0.008, 0.002-0.006, and 0.002-0.004 micrograms per square millimeter of implant surface area. The inventors believe these loading amounts to be significantly less than known for conventional drug eluting stents.

In preferred embodiments, implants of the present invention comprise strands as described in Table II coated with a conformal support coating 410, and further coated with a coating 210 comprising paclitaxel; wherein the strands comprise PLGA 88:12 (wt:wt), the support coating 410 comprises PLCL 50:50 (wt:wt) crosslinked with HDI and chain terminated with dodecanol, and the coating 210 comprises PLCL 70:30 (wt:wt) with paclitaxel incorporated therein. In such preferred embodiments: the diameter of the strands is about 150 microns, woven into a single fiber over 2 under 2 regular pattern; the thickness of the support coating 410 is 20-30 microns in thickness in the radial direction on individual strands, with a preferred maximum thickness of 250 microns at the braid nodes (i.e., where the strands overlap in the braid structure); and the thickness of coating 210 is about 3 microns.

The implant 100 of the present invention is preferably self-expanding in that it is manufactured at a first diameter, is subsequently reduced or "crimped" to a second, reduced diameter for placement within a delivery catheter, and self-expands towards the first diameter when extruded from the delivery catheter at an implantation site. The first diameter is preferably at least 10% larger than the diameter of the bodily lumen into which it is implanted. The implant 100 is preferably designed to recover at least about 80% and up to about 100% of its manufactured, first diameter. The inventors have found that implants in accordance with the present invention have a recovery diameter greater than 80%, and preferably greater than 90%, of the manufactured, first diameter after being crimped into exemplary delivery catheters of either 1.8 mm or 2.5 mm inner diameter and held for one hour at either room temperature (25° C.) or body temperature (37° C.).

The present invention is further described with reference to the following non-limiting examples.

Example 1

Braided implants were manufactured using a PLGA 12:88 (wt:wt) copolymer by spooling fiber spun monofilaments onto individual bobbins. Each bobbin was placed on a braiding machine, strung through rollers and eyelets and wrapped around a mandrel. The braiding tension of the machine was set for the size of the monofilament (i.e., 70 g min, 215 g max for 0.005" fiber). The pix/inch was set to obtain an ideal angle to maximize radial strength but still allow the braid to be removed from the mandrel (i.e., 110 to 135 degrees for a 6 mm mandrel). The braid pattern was selected and the monofilaments were braided off the spool onto the mandrel by the braiding machine. Tiewraps were used on the end of each mandrel to keep the tension on the filaments, which can be important for heat annealing and obtaining high modulus properties. The braided polymer was heat annealed on the mandrel, and then cut into desired lengths with a blade and removed from the mandrel. A representative implant was measured to have an outer diameter of about 6.0 mm and a length of about 20 mm.

Implants were coated with a support coating made from poly(glycolide-co-caprolactone) (PGCL) cured with hexamethylene diisocyanate. The PGCL 50:50 (wt:wt) copolymer was prepared as follows. A 100 mL round-bottom flask was dried in oven at 110° C. and then cooled to room temperature under a nitrogen atmosphere. The flask was charged with $Sn(Oct)_2$ (15 mg), pentaerythritol (68 mg), glycolide (10.0 g), and E-caprolactone (10.0 g), respectively. Subsequently, the flask was equipped with a magnetic stir bar and a three-way valve connected to a nitrogen balloon. The flask was thoroughly degassed under reduced pressure and flushed with nitrogen. The flask was then placed into an oil bath which was preheated to 170° C. The reaction was stirred at 170° C. for 24 h under a nitrogen atmosphere. After cooling to room temperature, the solid obtained was dissolved in dichloromethane and precipitated from anhydrous diethyl ether. The solution was decanted and the residual sticky solid was washed thoroughly with diethyl ether and dried in vacuum. Typically, around 18 g of polymer was recovered through the purification. GPC characterization revealed a number average molecular weight (Mn) of 39,900 and a polydispersity index (PDI) of 1.23.

The four-arm PGCL 50:50 (wt:wt) (1.0 g) and HDI (375 µL) were dissolved in 20 mL dichloromethane to make a stock solution for spray-coating. A steel mandrel of 2 mm in diameter was mounted vertically onto a mechanical stirrer, and the braided implant was placed over the mandrel. A spray gun (Badger 150) was arranged perpendicular to the mandrel, and connected to a nitrogen cylinder and a reservoir containing the stock solution. The mechanical stirrer was turned on to spin the mandrel and the solution was sprayed onto the braid by applying the nitrogen flow. The coating weight could be controlled by the spray time. After spray coating, devices were dried in air for 1 h and then cured at 100° C. for 16 h. A catalyst such as tin octanoate, zinc octanoate, aluminum tris (acetylacetonate), etc. may also be used in the curing process to reduce the curing time and/or temperature.

Example 2

Braided implants having an as-manufactured diameter of 6 mm were manufactured using a PLGA 79:21 (wt:wt) copolymer using a manufacturing process similar to that of Example 1. The implants were coated with a support coating made from PLCL 50:50 (wt:wt) prepared as follows. A 250 mL round-bottom flask was dried in an oven at 110° C. and cooled to room temperature in a nitrogen atmosphere. The flask was charged with $Sn(Oct)_2$ (11.5 mg), pentaerythritol (204 mg), lactide (30.0 g), and E-caprolactone (30.0 g), respectively. Subsequently, the flask was equipped with a magnetic stir bar and a three-way valve connected to a nitrogen balloon. The flask was thoroughly degassed under reduced pressure and flushed with nitrogen. The flask was then placed into an oil bath which was preheated to 170° C. The reaction was stirred at 170° C. for 48 h under a nitrogen atmosphere. After cooling to room temperature, the highly viscous liquid obtained was dissolved in approximately 200 mL dichloromethane and precipitated from 1200 mL anhydrous diethyl ether. The solution was decanted and the residual sticky polymer was washed thoroughly with diethyl ether and dried under vacuum. Typically, around 48 g polymer was recovered through the purification. GPC characterization revealed a number average molecular weight (Mn) of 52,500 and a polydispersity index (PDI) of 1.2.

Example 3

Braided implants having an as-manufactured diameter of 6 mm were manufactured using a PLGA 79:21 (wt:wt) copolymer using a manufacturing process similar to that of Example 1. The implants were coated with a support coating made from poly trimethylene carbonate (PTMC) and hexamethylenediisocyante. The PTMC three arm polymer was prepared as follows. A 100 mL round-bottom flask, previously dried under heat and vacuum, was charged with $Sn(Oct)_2$ (20 mg), triethanolamine (298.4 mg) and trimethylene carbonate (30 g) respectively. Subsequently, the flask was equipped with a magnetic stir bar and a three-way valve connected to a nitrogen balloon. The flask was thoroughly degassed under reduced pressure and flushed with nitrogen and then placed into an oil bath which was preheated to 70° C. The oil bath temperature was then increased to 100° C. over 15 minutes. The reaction was stirred at 100° C. for 23 h under a nitrogen atmosphere. After cooling to room temperature, the viscous liquid obtained was dissolved overnight in approximately 50 mL dichloromethane and subsequently precipitated from 550 mL ethanol. The precipitated polymer was stirred for one hour after which the ethanol was decanted. The process of dissolving the polymer in dichloromethane and precipitating in ethanol was repeated. The polymer was then dissolved in dichloromethane, precipitated into 550 mL diethyl ether and stirred for one hour after which time the diethyl ether was decanted. The polymer was then dried under vacuum at 70° C. for a period of 72 hours. Typically 24 g of polymer was recovered using above process. GPC characterization of the final polymer revealed a number average molecular weight (Mn) of 29 kDa and a polydispersity index (PDI) of 2.0.

Example 4

A support coating solution was prepared by dissolving 1.0 g of PLCL 50:50 (wt:wt) copolymer (Mn=67 kDa) in 19.875 mL of methlyene chloride. Subsequently, 0.125 mL of hexamethylene diisocyanate is added to the solution, which was then transferred to a 60 mL polypropylene syringe using a 14 gauge needle. No catalyst was added to the support coating solution at any time.

The support coating solution was sprayed onto PLGA 88:12 (wt:wt) braided implants. After spray coating, the implants were allowed to dry for up to 60 minutes in a nitrogen atmosphere. The implants were then transferred to a curing oven for a two-step curing process consisting of a first step at 75° C. for 16 hours, followed by a second step at 100° C. for a minimum of 96 hours.

Example 5

Braided tubular implants were prepared in accordance Example 1. The implants each comprised 32 strands of 88:12 (wt:wt) poly(L-lactic acid co-glycolic acid) copolymer (PLGA), braided into 7 mm diameter tubes. The strands had diameters of 0.006" and were woven in a single fiber over 2 under 2 regular pattern. The as-manufactured braided implants were coated with a conformal support coating comprising 50:50 (wt:wt) poly(lactic acid-co-caprolactone) copolymer (PLCL) crosslinked with hexamethylene diisocyanate. The support coating was 20-30 microns in thickness in the radial direction on individual strands, with a maximum thickness of about 250 microns at the braid nodes where the strands overlapped. The coated implants were further coated with an additional conformal coating comprising a mixture of PLCL 75:25 (wt:wt), and paclitaxel as therapeutic agent.

Figure 6:
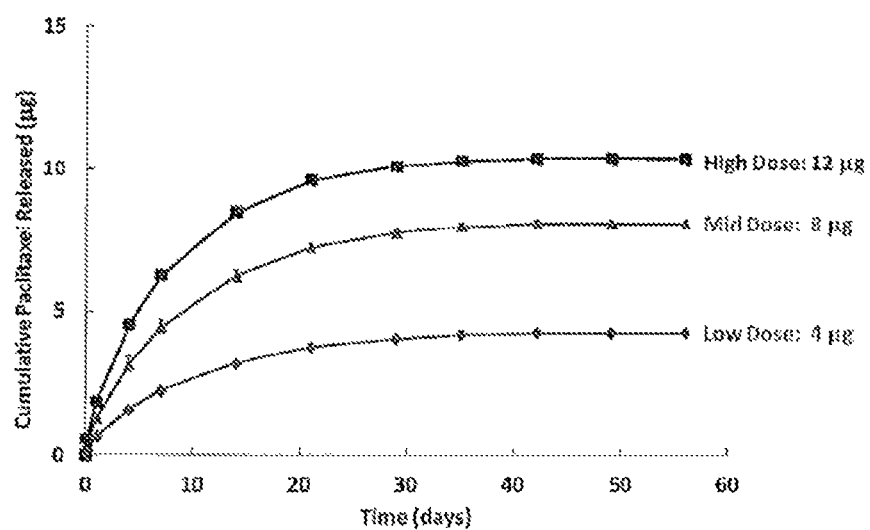
FIG. 6 shows the cumulative release over time of paclitaxel from the drug eluting implants of the present invention containing 12, 8 and 4 micrograms of paclitaxel.

In different samples, the amount of paclitaxel incorporated into the outermost coating, and thus carried by 27 mm long implants, was 4, 8 and 12 micrograms total or 0.003 micrograms, 0.007 microgram, and 0.010 micrograms per square millimeter of implant surface area, respectively. To assess the drug elution from the implants over time, these implants underwent simulated deployment through a delivery catheter and placed individually into a media of phosphate-buffered saline (PBS) at pH 7.4 containing a surfactant. The implants were conditioned for 63 days at 37° C. with mild agitation in order to simulate physiologic conditions. The media was analysed by HPLC at selected time points to determine the amount of paclitaxel eluting from the device coating over time. FIG. 6 shows the average cumulative paclitaxel eluting from the coated devices over time. After 7 days in release media, approximately 50% of the paclitaxel loaded on scaffolds eluted regardless of the drug dose. The total loading of paclitaxel in all scaffolds completely eluted within 42 days. No paclitaxel was detected in the media for 3 consecutive time points between 42 through 63 days. The devices were removed from the media at 63 days. After removal from the media, the devices were soaked in DCM to extract any residual paclitaxel. No un-released paclitaxel was detected on any of the devices, confirming that all paclitaxel had completely eluted.

Example 6

The implants of Example 5 were evaluated for device safety and vessel patency in sheep peripheral arteries. In different embodiments, 7×40 mm implants containing 4, 8, and 12 micrograms of paclitaxel (or 0.002 micrograms, 0.004 micrograms, and 0.007 micrograms per square millimeter of implant surface area, respectively) were implanted in the superficial femoral arteries (SFA) of five Suffolk Cross-bred sheep (80-100 Kg in weight). The profunda arteries (PFA) of these sheep were also implanted due to its close anatomic location with SFA. Bare implants (i.e., without any drug coating) were also implanted as control devices. The sheep were euthanized as planned at one month post implantation. The assessment included:

overall safety, as determined by device related animal deaths, adverse events (AEs), and overall animal health;
   vessel patency, defined as <50% mean diameter stenosis from two orthogonal angiography planes measured by quantitative vascular angiography (QVA);
   semi-quantitative histopathology assessments of treated vessels for device safety and biocompatibility.

All implants were successfully deployed without incidence of vessel dissection or thrombosis. During the one month in-life period, there were no animal deaths or AEs. The animal weight changes were as expected. Overall animal health remained normal throughout the study. Daily gait evaluation of the implanted animals showed no sign of abnormal gait behaviour. At necropsy, examination of all the external surfaces and orifices, especially the surface of the hind limbs; muscular/skeletal system; thoracic, abdominal and pelvic cavities with their associated organs and tissues; central nervous system (excluding brain) from every animal showed no evidence of abnormal findings.

Vessels implanted with all implants and bare controls were widely patent by QVA at one month post implantation.

Example 7

To determine the in-vivo drug release of the implants of the present invention, the three formulations of Example 5 were implanted in the superficial femoral arteries (SFA) or profunda arteries (PFA) of Suffolk Cross-bred sheep (80-100 Kg in weight). Devices were explanted at 1 day, 7 days, and 30 days.

Explanted vessels containing the implants were cut into slices and placed in vials. Paclitaxel remaining in the explanted slices was extracted by soaking in DCM. The extracted samples were purified using a methanol precipitation and analysed using an HPLC to quantify the amount of paclitaxel remaining on each device and attached tissue. The amount of paclitaxel eluted from each device was calculated from the known initial paclitaxel loading and the measured amount remaining on the scaffold and attached tissue.

Although the implants containing 8 and 12 micrograms of paclitaxel were loaded with 2 and 3 times the amount of paclitaxel as those implants containing 4 micrograms, the relative percentage of paclitaxel eluted over time was approximately equivalent. Approximately 50% of the loaded paclitaxel eluted after 7 days and 98% eluted after 30 days in-vivo, independent of the initial paclitaxel load.

The elution of paclitaxel from the implants tested in-vitro is most rapid immediately after initiation drug release testing. At relatively longer time points, 7 and 30 days, there is good agreement between the amount of paclitaxel eluting from the scaffold in-vivo and in-vitro for all three doses. This suggests that the in-vitro release assessment accurately predicts the approximate amount of paclitaxel released from the scaffold after implantation.

Summary of Examples 6-7

In all animals treated with implants of the present invention, there were no device related animal deaths, AEs and animal health remained normal. All implants were deployed as expected and all treated vessels were patent. Histology analyses of implanted vessels showed paclitaxel dose dependent tissue responses with normal tissue healing in all three paclitaxel doses at one month post implantation. In-vivo drug release results correlated well in-vitro drug release results. Plasma PK analysis demonstrated non-detectable levels of systemic paclitaxel content. These animal study results support the safety and performance of the implants.

The present invention provides woven and non-woven self-expanding medical implants for placement within a bodily lumen that have sufficient strength and other mechanical properties that are necessary to effectively treat a variety of medical conditions. While aspects of the invention have been described with reference to example embodiments thereof, it will be understood by those skilled in the art that various changes in form and details may be made therein without departing from the scope of the invention.

We claim:

1. A medical implant comprising: a tubular structure comprising polymeric strands and open spaces between adjacent said polymeric strands, said polymeric strands comprising a first polymeric material; a first conformal coating at least partially coating said polymeric strands; and a second conformal coating at least partially coating said first conformal coating and comprising a second polymeric material and an amount of paclitaxel as a single therapeutic agent in said medical implant; wherein each of said polymeric strands has a cross-sectional diameter within the range of about 0.003 to about 0.007 inches, wherein said tubular structure is characterized by a surface area, and the amount of paclitaxel is within the range of about 0.002 to about 0.175 micrograms per square millimeter of said surface area.

2. The medical implant of claim 1, wherein said tubular structure comprises at least 32 strands.

3. The medical implant of claim 2, wherein the amount of paclitaxel is within the range of about 0.002 to about 0.09 micrograms per square millimeter of said surface area.

4. The medical implant of claim 1, wherein said tubular structure comprises at least 24 strands.

5. The medical implant of claim 4, wherein the amount of paclitaxel is within the range of about 0.003 to about 0.12 micrograms per square millimeter of said surface area.

6. The medical implant of claim 1, wherein said tubular structure comprises at least 16 strands.

7. The medical implant of claim 6, wherein the amount of paclitaxel is within the range of about 0.004 to about 0.175 micrograms per square millimeter of said surface area.

8. The medical implant of claim 1, wherein said tubular structure comprises a total amount of paclitaxel within the range of about 0.1 to about 2.0 micrograms per millimeter of length of said tubular structure.

9. The medical implant of claim 1, wherein said tubular structure comprises a total amount of paclitaxel within the range of about 0.2 to about 2.0 micrograms per millimeter of length of said tubular structure.

10. The medical implant of claim 1, wherein said second conformal coating has a thickness up to 8 microns.

11. The medical implant of claim 1, wherein the amount of paclitaxel is within the range of about 0.002 to about 0.02 micrograms per square millimeter of said surface area.

12. The medical implant of claim 11, wherein said tubular structure comprises between about 16 and about 32 strands.

13. The medical implant of claim 12, wherein the first polymeric material is poly(lactic acid co-glycolic acid), wherein said first conformal coating comprises crosslinked poly(lactic acid-co-caprolactone) and wherein said second polymeric material is poly(lactic acid-co-caprolactone) that is not crosslinked.

14. A medical implant comprising: a tubular structure comprising polymeric strands and open spaces between adjacent said polymeric strands, said polymeric strands comprising a first polymeric material; a first conformal coating at least partially coating said polymeric strands; and a second conformal coating at least partially coating said first conformal coating and comprising a second polymeric material and an amount of paclitaxel as a single therapeutic agent in said medical implant; wherein said tubular structure is characterized by a surface area, wherein the amount of paclitaxel is within the range of about 0.002 to about 0.175 micrograms per square millimeter of said surface area, and wherein said tubular structure has a surface area within the range of about 11.4 to about 53.8 square millimeters per millimeter of length of said tubular structure.

15. The medical implant of claim 14, wherein said tubular structure comprises a total amount of paclitaxel within the range of about 0.1 to about 2.0 micrograms per millimeter of length of said tubular structure.

16. The medical implant of claim 14, wherein said tubular structure comprises a total amount of paclitaxel within the range of about 0.2 to about 2.0 micrograms per millimeter of length of said tubular structure.

17. The medical implant of claim 14, wherein the amount of paclitaxel is within the range of about 0.002 to about 0.02 micrograms per square millimeter of said surface area.

18. The medical implant of claim 17, wherein said tubular structure comprises between about 16 and about 32 strands.

19. The medical implant of claim 18, wherein the first polymeric material is poly(lactic acid co-glycolic acid), wherein said first conformal coating comprises crosslinked poly(lactic acid-co-caprolactone) and wherein said second polymeric material is poly(lactic acid-co-caprolactone) that is not crosslinked.

20. A medical implant comprising: a tubular structure comprising between 16 and 32 polymeric strands woven into together to form said tubular structure, each of said polymeric strands having a cross-sectional diameter within the range of about 0.003 to about 0.007 inches; a conformal coating at least partially coating said polymeric strands and comprising an amount of paclitaxel as a single therapeutic agent in said medical implant; wherein said tubular structure is characterized by a surface area within the range of about 11.4 to about 53.8 square millimeters per millimeter of length of said tubular structure, and the amount of said paclitaxel is within the range of about 0.002 to about 0.175 micrograms per square millimeter of said surface area.

21. The medical implant of claim 20, wherein the amount of paclitaxel is within the range of about 0.002 to about 0.02 micrograms per square millimeter of said surface area.

* * * * *